United States Patent
Bender

(10) Patent No.: US 10,558,667 B2
(45) Date of Patent: *Feb. 11, 2020

(54) SYSTEM AND METHOD OF HEALTHCARE DATA MANAGEMENT

(71) Applicant: NaviNet, Inc., Boston, MA (US)

(72) Inventor: Ryan Bender, Vienna, VA (US)

(73) Assignee: NaviNet, Inc., Boston, MA (US)

( * ) Notice: Subject to any disclaimer, the term of this patent is extended or adjusted under 35 U.S.C. 154(b) by 534 days.

This patent is subject to a terminal disclaimer.

(21) Appl. No.: 15/213,917

(22) Filed: Jul. 19, 2016

(65) Prior Publication Data

US 2016/0328447 A1 Nov. 10, 2016
US 2017/0206248 A9 Jul. 20, 2017

Related U.S. Application Data

(63) Continuation of application No. 12/700,477, filed on Feb. 4, 2010, now Pat. No. 9,430,612.

(60) Provisional application No. 61/149,878, filed on Feb. 4, 2009.

(51) Int. Cl.
*G06F 16/2455* (2019.01)
*G06F 16/27* (2019.01)
*G06F 8/65* (2018.01)
*G06Q 50/24* (2012.01)

(52) U.S. Cl.
CPC ............ *G06F 16/2455* (2019.01); *G06F 8/65* (2013.01); *G06F 16/27* (2019.01); *G06Q 50/24* (2013.01)

(58) Field of Classification Search
None
See application file for complete search history.

(56) References Cited

U.S. PATENT DOCUMENTS

| 5,701,461 A | 12/1997 | Dalal |
| 7,343,586 B1 | 3/2008 | Hernandez |
| 2003/0018719 A1* | 1/2003 | Ruths ............. G06F 9/52 709/205 |
| 2005/0071194 A1* | 3/2005 | Bormann ........ G06F 17/30578 705/2 |
| 2007/0067186 A1 | 3/2007 | Brenner et al. |
| 2007/0234331 A1 | 10/2007 | Schow |
| 2007/0288427 A1 | 12/2007 | Ramer |
| 2010/0088693 A1* | 4/2010 | Vulugundam ............ G06F 8/65 717/173 |

OTHER PUBLICATIONS

Alexander Stage, "Synchronization and replication in the context of mobile applications" Nov. 15, 2001 (Year: 2001).*

* cited by examiner

*Primary Examiner* — Paul R Fisher
(74) *Attorney, Agent, or Firm* — Stetina Brunda Garred and Brucker

(57) ABSTRACT

A method of managing healthcare data is disclosed. Healthcare data of the first healthcare database operated by a first healthcare data management system (HDMS) is collected. The collected healthcare data is stored in a second healthcare database operated by the second HDMS. The healthcare data between the first healthcare database and the second healthcare database are synchronized by detecting a change in the healthcare data of the first healthcare database, creating a delta file representing the change in the healthcare data of the first healthcare database, transmitting the delta file to the second HDMS and updating the healthcare data of the second healthcare database based on the delta file.

20 Claims, 6 Drawing Sheets

SYSTEM AND METHOD OF HEALTHCARE DATA MANAGEMENT

CROSS-REFERENCE TO RELATED APPLICATIONS

This application claims priority under 35 U.S.C. § 120 from U.S. patent application Ser. No. 12/700,477, filed on Feb. 4, 2010, which claims priority to U.S. Provisional Application No. 61/149,878 filed on Feb. 4, 2009, the disclosures of which are incorporated herein in their entirety by reference.

BACKGROUND OF THE INVENTIVE CONCEPT

1. Field of the Invention

The disclosure is directed generally to a system and method for healthcare data management and, more particularly to, managing healthcare data in a healthcare data network (HDN) using a data management agent (MDA).

2. Description of the Related Art

Healthcare firms are constantly seeking to reduce costs, streamline operations and improve patient care as the industry continues to deal with a challenging and constantly evolving business environment. In addition, the regulatory requirements of the U.S. Government HIPAA statutes are driving significant and long-term changes to the IT infrastructure for carrying out administrative tasks and patient care. For these reasons, the healthcare industry is looking to automation to play a major role in controlling costs and improving operations.

The healthcare industry's typical IT infrastructure is a complex assembly of packaged administrative applications together with packaged and custom healthcare-specific applications. While manual and paper processes have been gradually automated, the volume of data that hospitals and healthcare networks must manage and process has been growing at an exponential rate. Because healthcare IT systems support crucial clinical operations and current data must be available at all times, always on, zero-latency healthcare management and synchronization applications are becoming increasingly important.

SUMMARY OF THE INVENTIVE CONCEPT

According to an aspect of the disclosure, a method of managing healthcare data includes collecting healthcare data of the first healthcare database operated by the first healthcare data management system (HDMS). The collected healthcare data is stored in the second healthcare database operated by the second HDMS. The healthcare data is synchronized between the first healthcare database and the second healthcare database by detecting a change in the healthcare data of the first healthcare database, creating a delta file representing the change in the healthcare data of the first healthcare database, transmitting the delta file to the second HDMS, and updating the healthcare data of the second healthcare database based on the delta file.

The method may further include controlling the first HDMS remotely from the second HDMS. The method may further include transmitting a command file to the first HDMS for execution and remotely controlling the first HDMS to execute the command file.

The method may further include transmitting a database query to the first HDMS for execution and remotely controlling the first HDMS to execute the database query against the first healthcare database.

The method may further include transmitting system information of the first HDMS to the second HDMS, selecting one or more patch files for the first HDMS based on the system information, transmitting the one or more patch files to the first HDMS for execution, and remotely controlling the first HDMS to install the one or more patch files in the first HDMS.

The delta file may include minimum information necessary to synchronize the healthcare data between the first healthcare database and the second healthcare database. The first HDMS may be configured to manage the healthcare data for one or more local healthcare facilities, and the second HMS may be configured to manage the healthcare data for a central healthcare data center. The method may further include disallowing transmission of the healthcare data of the second HDMS to the first HDMS.

The method may further include installing a data management agent (DMA) to the first HDMS. The DMA may be configured to perform at least one of the synchronizing of the healthcare data and allowing the second HDMS to remotely control the first HDMS to at least one of execute a command file, execute a query against the first healthcare database and optimize a configuration of the first HDMS.

According to another aspect of the disclosure, a healthcare data network includes the first healthcare data management system (HDMS) configured to operate the first healthcare database storing healthcare data, the first HDMS operating a data management agent (DMA), and the second HDMS configured to operate the second healthcare database storing the healthcare data collected from the first healthcare database. The DMA is configured to detect a change in the healthcare data of the first healthcare database, create a delta file representing the change in the healthcare data of the first healthcare database and transmit the delta file to the second HDMS via the network.

The delta file may include minimum information necessary to synchronize the healthcare data between the first healthcare database and the second healthcare database. The second HDMS may be further configured to update the healthcare data of the second healthcare database based on the delta file transmitted from the first HDMS.

The DMA may be further configured to operate in a background without user intervention. The DMA may be further configured to disallow transmission the healthcare data of the second healthcare database to the first healthcare database.

The DMA may be further configured to allow the second HDMS to remotely control the first HDMS. The first HDMS may be remotely controlled by the second HDMS to execute a command file transmitted from the second HDMS. The first HDMS may be remotely controlled by the second HDMS to execute a database query transmitted from the second HDMS against the first healthcare database.

The DMA may be further configured to transmit system information of the first HDMS to the second HDMS, download one or more patch files for the first HDMS from the second HDMS, and install the one or more patch files in the first HDMS. The one or more patch files may be selected by the second HDMS based on the system information.

The healthcare data may include at least one of personal information, medical records, healthcare provider information, healthcare insurance information, appointment information, diagnosis information, treatment information and prescription information of a patient.

Additional features, advantages, and embodiments of the disclosure may be set forth or apparent from consideration of the following attached detailed description and drawings. Moreover, it is to be understood that both the foregoing summary of the disclosure and the following attached detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION OF THE PREFERRED EMBODIMENTS

Figure 1:
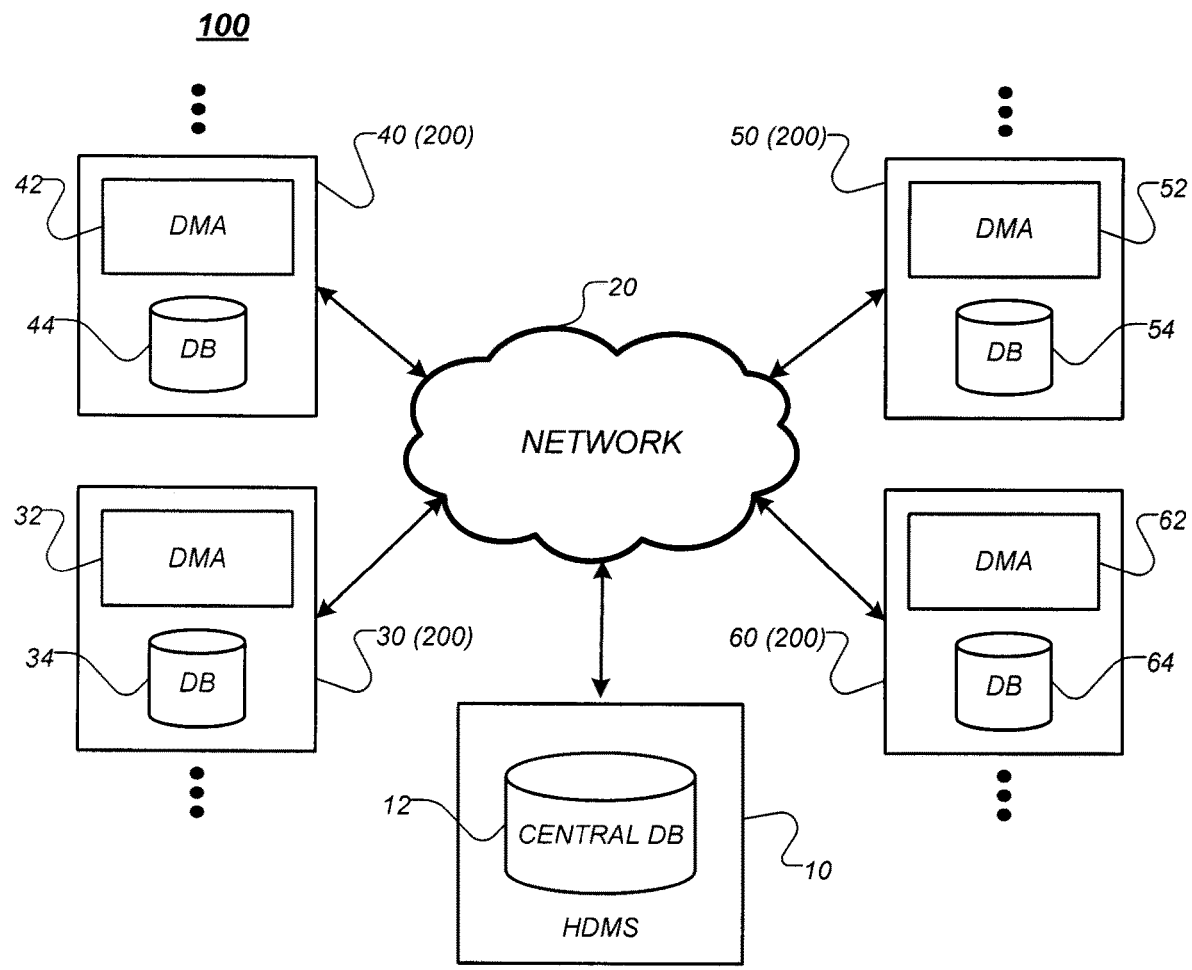
FIG. 1 shows a conceptual overview of a healthcare data network (HDN) constructed according to the principles of the disclosure.

The embodiments of the disclosure and the various features and advantageous details thereof are explained more fully with reference to the non-limiting embodiments and examples that are described and/or illustrated in the accompanying drawings and detailed in the following attached description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

FIG. 1 shows a conceptual overview of a healthcare data network (HDN) 100 constructed according to the principles of the disclosure. Various operations of the HDN 100 is set forth in detail in U.S. application Ser. No. 11/525,124, filed Sep. 22, 2006 and titled "METHOD AND SYSTEM FOR ELECTRONICALLY PRESCRIBING MEDICATIONS," which is expressly incorporated herein by the reference in its entirety.

The HDN 100 may include a central healthcare data management system (HDMS) 10 and at least one local healthcare data management system (HDMS), such as, e.g., local HDMS 30, 40, 50, 60 and the like. Each of the local HDMS 30, 40, 50, 60 may be connected to the central HDMS 10 via a network 20 to communicate data. The network 20 may be any one or more of the Internet, a local area network (LAN), a wide area network (WAN), a metropolitan area network (MAN), a personal area network (PAN), a campus area network, a corporate area network, a global area network, a broadband area network (BAN), a cellular data network and/or the like, any of which may be configured to communicate data via a wireless and/or a wired communication medium.

The local HDMS 30, 40, 50, 60 may include, for example, any combination of software and/or hardware capable of accepting data, performing prescribed mathematical and logical operations and output the result of these operations. For example, the local HDMS 30, 40, 50, 60 may be a computer (e.g., a desktop computer, a laptop computer, a mobile computer, a netbook, a tablet PC or the like), a personal data assistant (PDA), a mobile telephone, a cloud computing configuration and/or the like. The local HDMS 30, 40, 50, 60 may run one or more applications, such as, e.g., a healthcare practice management application (HPMA), a database management system application (DBMS) and/or the like to manage local healthcare databases 34, 44, 54, 64, respectively.

Each of the local healthcare databases 34, 44, 54, 64 may store healthcare data for one or more healthcare facilities, such as, e.g., a general hospital, a specialized hospital, a clinic, a physician's office, a dentist's office, a dental specialist's office, a veterinarian's office, an optometrist's office, a chiropractor's office, a podiatrist's office, a psychologist's office, a physical therapist's office, a pharmacy, a surgical center and/or the like. The healthcare data may include at least one of personal information, medical record, healthcare provider information, healthcare insurance information, appointment information, diagnosis information, treatment information, prescription information and/or the like of one or more patients of the healthcare facility. The local healthcare databases 34, 44, 54, 64 may include a structured collection of the healthcare data organized according to a database model, but not limited to at least one of a relational model, a hierarchical model, a network model, or the like. The healthcare data stored in the local healthcare databases 34, 44, 54, and 64 may be organized into data files corresponding to one or more individual patients.

The central HDMS 10 may be configured to manage a central healthcare database 12 for, e.g., a central healthcare data center for the HDN 100. The central healthcare database 12 may store the healthcare data collected from the local healthcare databases 34, 44, 54, 64. The central HDMS 10 may include, for example, any combination of software and/or hardware capable of accepting data, performing prescribed mathematical and logical operations and output the result of these operations. For example, the central HDMS 10 may be a server configured to run at least one application, such as, e.g., a DBMS to manage the central healthcare database 12, often under heavy workloads, unattended, for extended periods of time with minimal human direction. Additionally, the HDMS 10 may be configured, at least in part, using a cloud computing configuration. The central healthcare database 12 may include a structured collection of the healthcare data collected from the local healthcare databases 34, 44, 54, 64. The central healthcare database 12 may be organized according to a database model, but not limited to at least one of a relational model, a hierarchical model, a network model and the like.

The HDN 100 may be configured to perform various functions, such as, e.g., remote data synchronization, remote command execution, remote database queries, remote local HDMS configuration and/or the like, which are described below in detail with reference to FIGS. 3-6. To carry out those functions, the local HDMS 30, 40, 50, 60 may include data management agents (DMA) 32, 42, 52, 62, respectively. In an embodiment, each of the DMA 32, 42, 52, 62 may be an application that runs in the background to carry out the various functions without user intervention. For example, for a system running on a Microsoft Windows™ operating system, the DMA may be implemented as a Windows service application. For a Linux™/Unix™ based system, the DMA may be implemented as a daemon, as known in the art. The DMA may be a relatively small file, which may be downloaded from the central HDMS 10 or other online data storage via the network 20.

Figure 2:
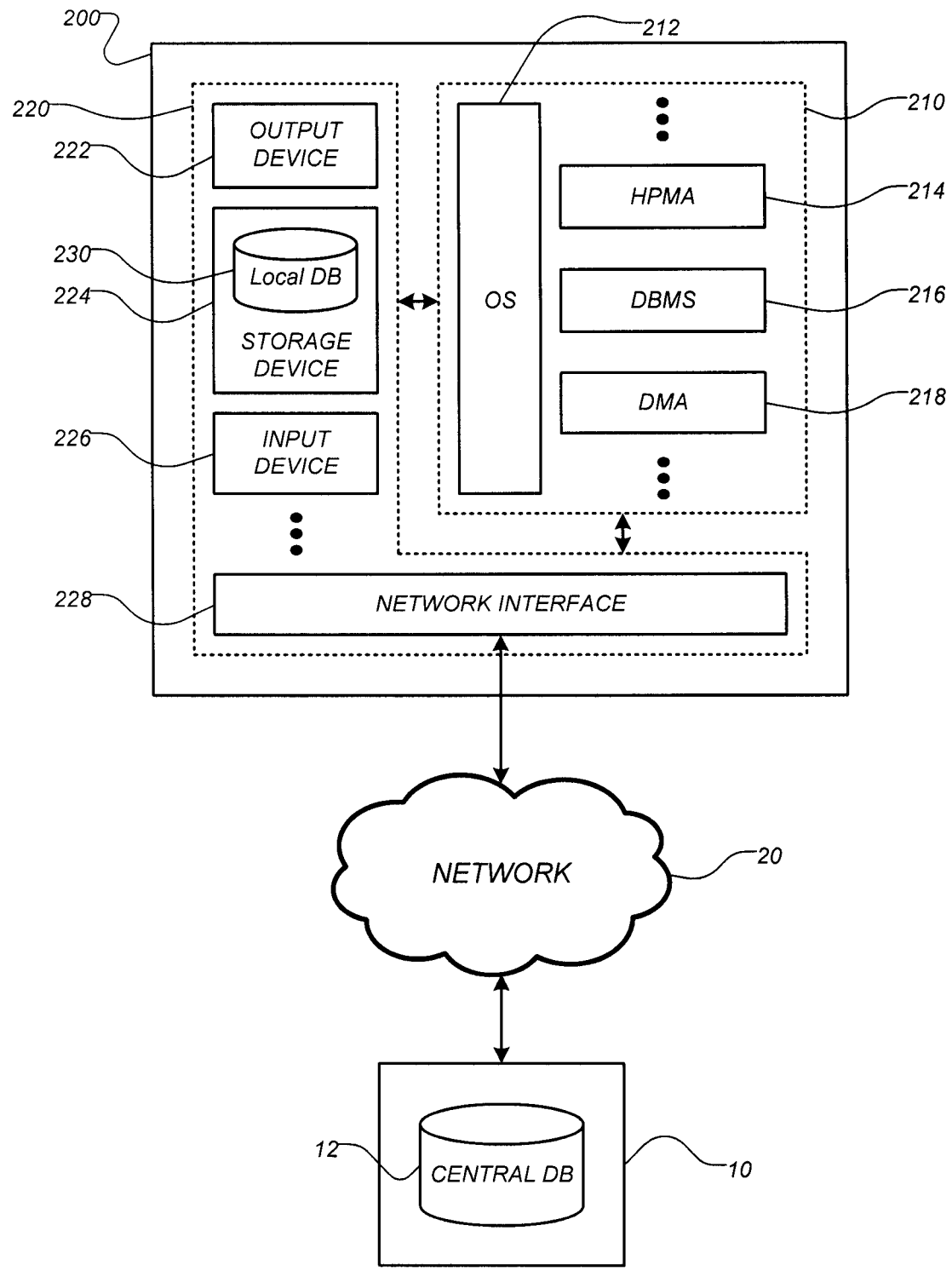
FIG. 2 shows a detailed view of a local healthcare data management system (HDMS) connected to a central HDMS via a network, constructed according to the principles of the disclosure.

FIG. 2 shows a detailed view of a local HDMS 200 connected to the central HDMS 10 via the network 20, constructed according to the principles of the disclosure. The local HDMS 200 may be any of the local HDMS 30, 40, 50, 60 shown in FIG. 1. As noted above, the local HDMS 200 may be a combination of software 210 and hardware 220. The software 210 may include an operating system (OS) 212, one or more applications, such as, e.g., a healthcare practice management application (HPMA) 214, a database management system application (DBMS) 216, a data management agent (DMA) 218 and/or the like. The hardware 220 may include one or more output devices 222 (e.g., a monitor, a speaker, a printer and/or the like), one or more storage devices (e.g., a hard disk drive, a network drive, an online storage device, a floppy disk drive, a flash memory device and/or the like), one or more input device (e.g., a keyboard, a mouse, a microphone, a fingerprint reader, a camera and/or the like), a network interface (e.g., a LAN card, a wireless network adaptor and/or the like) and/or the like.

As well known in the art, the OS 212 may function as an interface between the hardware 220 and a user, and carry out activity management and coordination, resource sharing and/or the like for of the local HDMS 200 while acting as a host for the applications, such as, the HPMA 214, the DBMS 216, the DMA 218 and/or the like. The OS 212 may include one or more of Microsoft Windows™, Mac OS™, Solaris™, Linux™/Unix™, OS/2™, BeOS™, AmigaOS4™, RISC OS™ and/or the like.

The HPMA 214 may be any commercially or non-commercially available application for electronically managing healthcare data for one or more healthcare facilities, such as, e.g., eClinicalWorks™ by EaseMD Systems™, Healthmatics Ntierprise™ by Allscripts™, MedicsElite™ by Advanced Date Systems™ or the like. For example, a user, such as, e.g., a physician, a nurse, an administrative staff and/or the like, may use the HPMA 214 to update the healthcare data, such as, e.g., personal information, healthcare provider information, appointment information, diagnosis information, treatment information and prescription information and/or the like of the patients. The healthcare data may be categorized and structurally arranged in a local database 230, which may be stored in the storage device 224 and managed by the DBMS 216.

As noted above, the DMA 218 may carry out various operations for the HDN 100, such as, e.g., remote data synchronization, remote command execution, remote database queries, remote local HDMS configuration and/or the like. The DMA 218 may be a background application operating without user intervention. As shown in FIG. 2, the DMA 218 may be provided in addition to and operate independently from the HPMA 214. Accordingly, the DMA 218 may carry out the various operations even when each of the HDMS 30, 40, 50, 60 runs a different HPMA 214 for healthcare data management.

Figure 3:
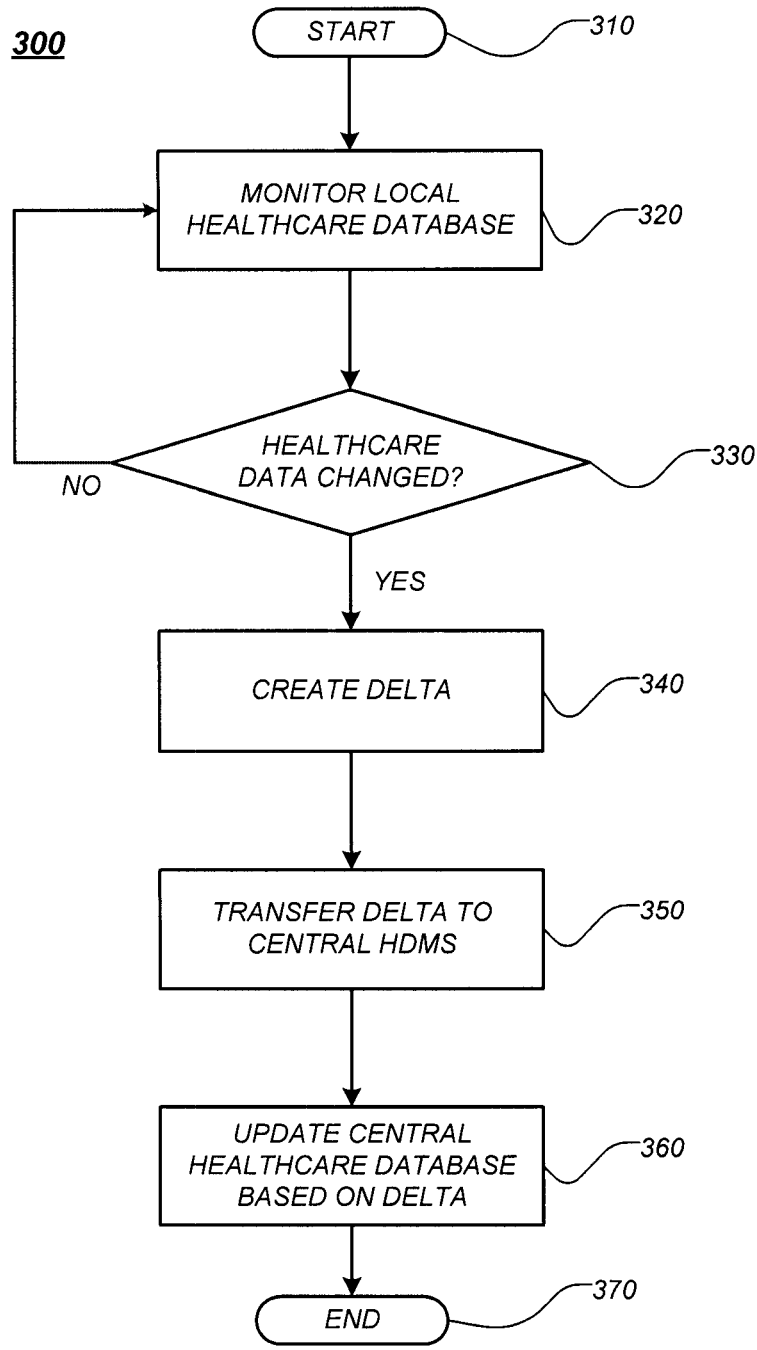
FIG. 3 shows a flowchart of a remote synchronization process according to the principles of the disclosure.

FIG. 3 shows a flowchart of a remote synchronization process 300 in the HDN 100 according to the principles of the disclosure. With reference to FIG. 2, the process 300 may start (at 310) when the DMA 218 is operating in the background of the local HDMS 200 to allow the central HDMS 10 to control the local HDMS 200 remotely using the DMA 218. The DMA 218 may monitor the local healthcare database 230 (at 320) to detect changes in the local healthcare database 230. In an embodiment, the DMA 218 may be configured to detect the changes to the healthcare database 230 in a real-time basis. Alternatively, the DMA 218 may be configured to periodically inspect the local healthcare database 230 and collect the changes that occurred during each inspection cycle. When no change is detected in the local healthcare database 230 (NO at step 330), the DMA 218 may continue to monitor the local healthcare database 230 (at step 320).

When a patient's healthcare data has been changed, for example, when a patient has a new phone number, switched to a new healthcare provider, changed healthcare insurance, has been diagnosed, treated and/or prescribed and/or the like, a user of the local HDMS 200 may use the HPMA 214 to update a data file corresponding to the patient's healthcare data stored in the healthcare database 230, thereby causing a change to the healthcare database 230. Upon detecting the change in the data file in the healthcare database 230 (YES at step 330), the DMA 218 may create a delta file representing the change to the local healthcare database 230 (at step 340). The delta file may contain minimum information necessary to maintain synchronization between the local healthcare database 230 and the central healthcare database 12. Thus, the delta file may be relatively small in size and created promptly without using significant system resources of the HDMS 200. The delta file created by the DMA 218 may be transferred from the local HDMS 200 to the central HDMS 10 via the network (at 350). The corresponding healthcare data of the patient stored in the central healthcare database 12 may be updated based on the delta file (step 360) to synchronize the local healthcare database 230 and the central healthcare database 12, and the process 300 may terminate (at 370). Thus, it may not be necessary to transfer the entire data file corresponding to the patient's healthcare data.

Accordingly, the local healthcare database 230 and the central healthcare database 12 may be synchronized in a timely manner without requiring extra infrastructures (e.g., software application, increased bandwidth, more processing power and/or the like). In an aspect, the DMA 218 may be configured to prevent the local HDMS 200 from accessing (e.g., downloading) the healthcare data stored in the central healthcare database 12, including the healthcare data uploaded from the local HDMS 200 itself such that all data transmission may flow one-way from the local HDMS 200 to the central HDMS 10. Since the local HDMS 200 and the central HDMS 10 may be synchronized by the one-way transmission of delta files, there may be no need to allow other computers to access to the local HDMS 200 and the central HDMS 10. Accordingly, the HDN 100 may be less vulnerable to attacks from online hackers and intruders.

Figure 4:
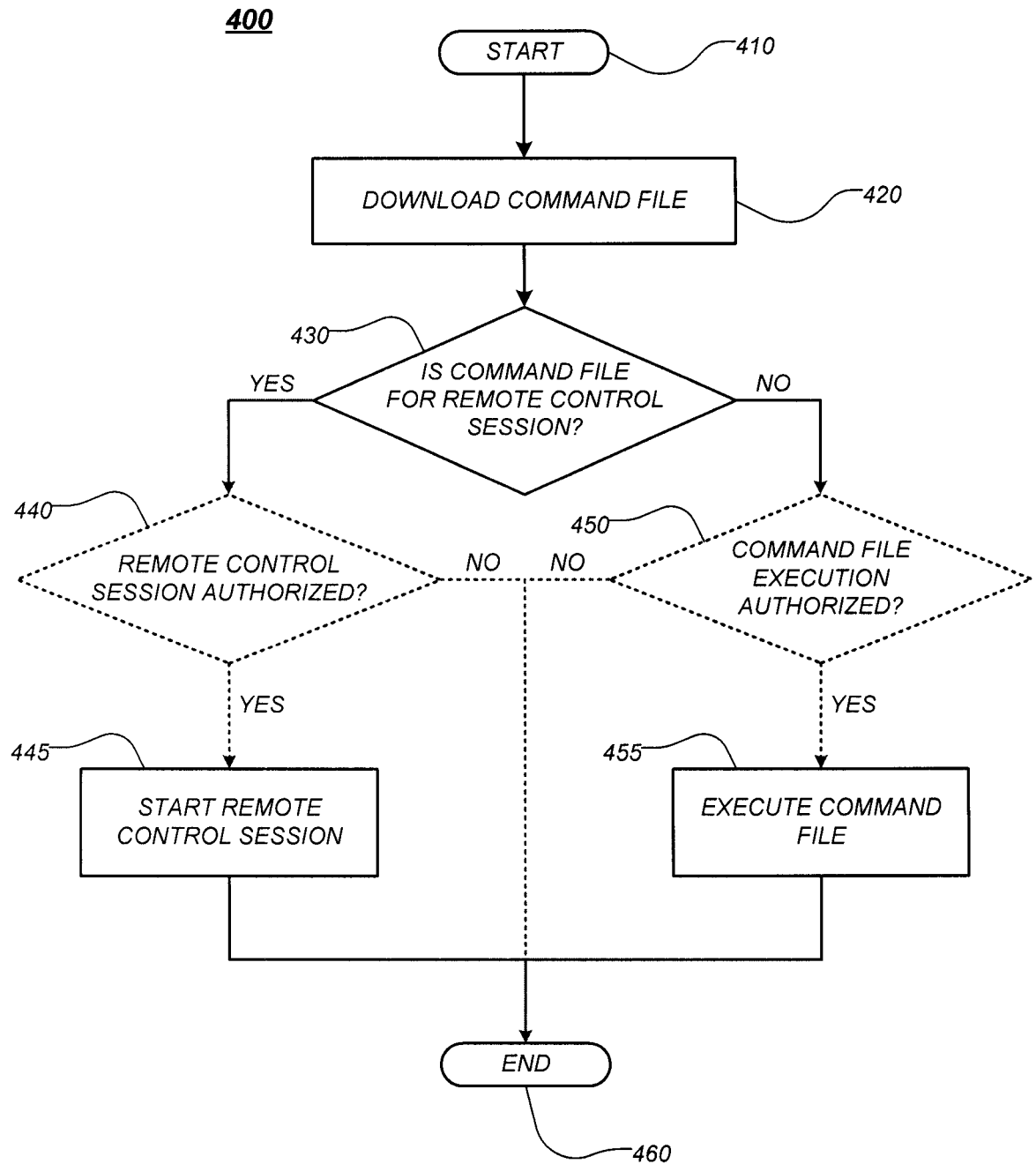
FIG. 4 shows a flowchart of a remote command execution process according to the principles of the disclosure.

FIG. 4 shows a flowchart of a remote command execution process 400 according to the principles of the disclosure. With reference to FIG. 2, the process 400 may start (at 410) when the DMA 218 is running in the background of the local HDMS 200 and in communication with the DMA 218 to allow the central HDMS 10 to remotely control the local HDMS 200 using the DMA 218. When the central HDMS 10 has a command file to be locally executed in the local HDMS 200, the central HDMS 10 may send the DMA 218 a notification regarding the command file. In response to the notification, the DMA 218 may operate the local HDMS 200 to download the command file from the central HDMS 10 or an alternative network storage location (at 420). The downloaded command file may be stored in the storage device 224 of the local HDMS 200.

The downloaded file may be any computer file that may be executed in the local HDMS 200. For example, the downloaded file may be for operating one or more output devices 222 to print a document, display a message on the display and/or the like. Alternatively, the downloaded command file may be for initiating a remote control session such that a person can control the local HDMS 200 remotely from the central HDMS 10 for, e.g., technical assistance, system calibration, and/or the like. When the downloaded command file is for initiating a remote control session (YES at 430), the DMA 218 may control the local HDMS 200 to execute the command file to initiate a remote control session between the local HDMS 200 and the central HDMS 10 (at 445). Upon completing the remote control session, the process 400 may terminate (at 460).

Optionally, before executing the downloaded command file, the DMA 218 may control the local HDMS 200 to acquire authorization for the remote control session from a user of the local HDMS 200 by, for example, displaying a message on the screen thereof or the like. In this case, the DMA 218 may control the local HDMS 200 to initiate the remote control session (at 445) only when the remote control session is authorized by the user (YES at 440). The process 400 may terminate (at 460) when the user does not authorize the remote control session (NO at 440)

When the downloaded command file is not for initiating a remote control session (NO at 430), the DMA 218 may control the local HDMS 200 to execute the command file locally (at 455) and the process 400 may terminate (at 460). Alternatively, the DMA 218 may control the local HDMS 200 to acquire authorization for execution of the command file from a user of the local HDMS 200 by, for example, displaying a message on the screen thereof or the like. The command file may be executed (at 455) when the user authorizes the execution of the command file (YES at 450). When the execution of the command file is not authorized by the user (NO at 450), the process 400 may terminate (at 460).

Figure 5:
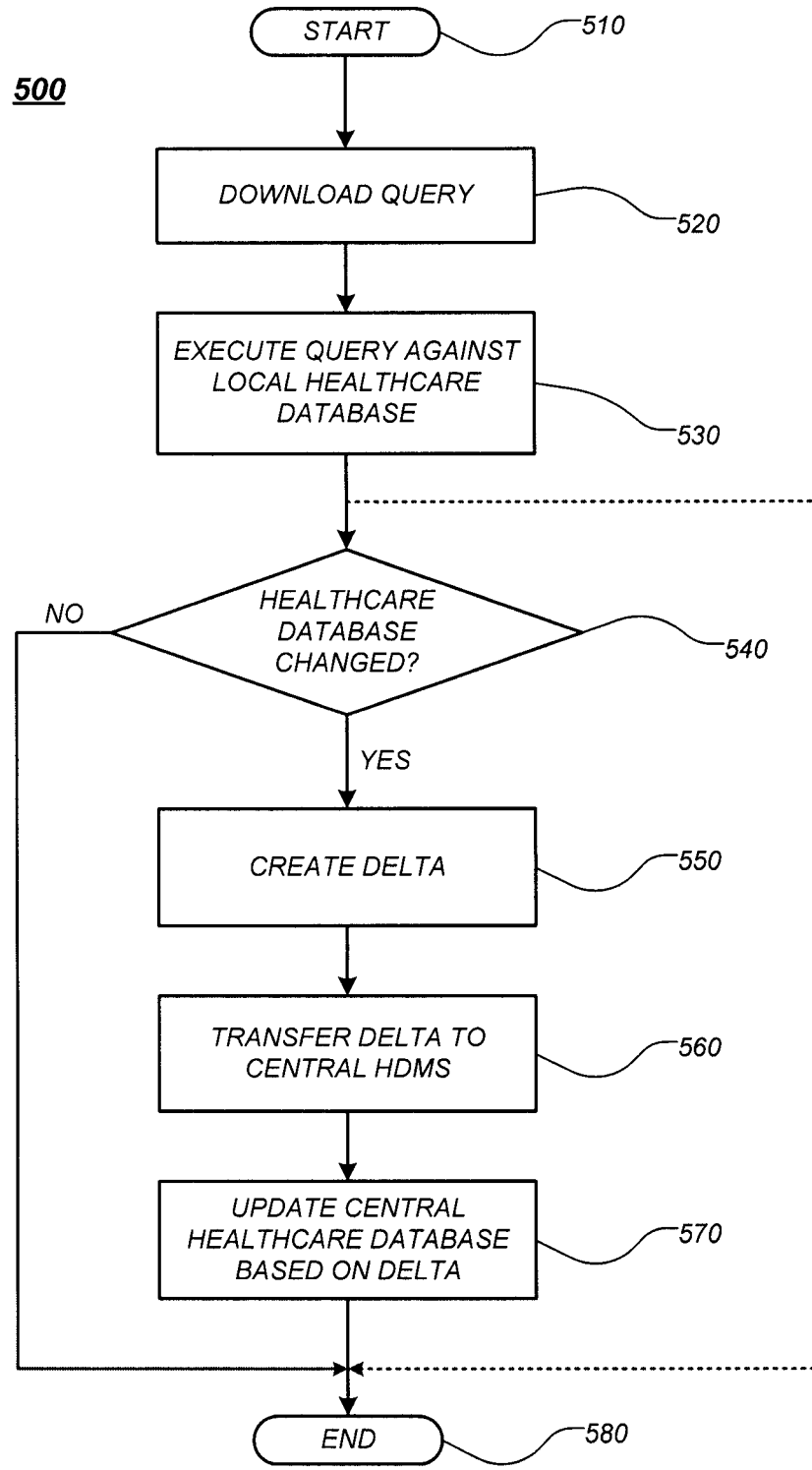
FIG. 5 shows a flowchart of a remote database query process according to the principles of the disclosure.

FIG. 5 shows a flowchart of a remote database query process 500 according to the principles of the disclosure. With reference to FIG. 2, the process 500 may start (at 510) when the DMA 218 is running in the background of the local HDMS 200 to allow the central HDMS 10 to control the local HDMS 200 remotely using the DMA 218. The central HDMS 10 may send the DMA 218 an instruction to download a query, such as, e.g., a SQL query, a connection string and/or the like, via open database connectivity (ODBC), direct connection and/or the like, for execution against the local healthcare database 230. In response, the DMA 218 may download the query from the central HDMS 10 or an alternative data storage location (at 520). The downloaded query may be executed against the local database 230 (at 530). The process 500 may terminate (at 580) upon executing the query (at 530) as indicated by a dotted line in FIG. 5.

Alternatively, the DMA 218 may determine whether the local healthcare database 230 has been changed (at 540) after the query has been executed (at 520). When there is no change in the local healthcare database 230 (NO at 540), the process 500 may terminate (at 580). When the local healthcare database 230 has been changed (YES at 540), the DMA 218 may carry out the remote synchronization process 300 shown in FIG. 3. For example, the DMA 218 may create one or more delta files (at 550) and transfer the delta files to the central healthcare database 12 via the network (at 560). The central healthcare database 12 may be updated based on the delta files received from the local HDMS 200 (at 570) and the process 500 may terminate (at 580).

Figure 6:
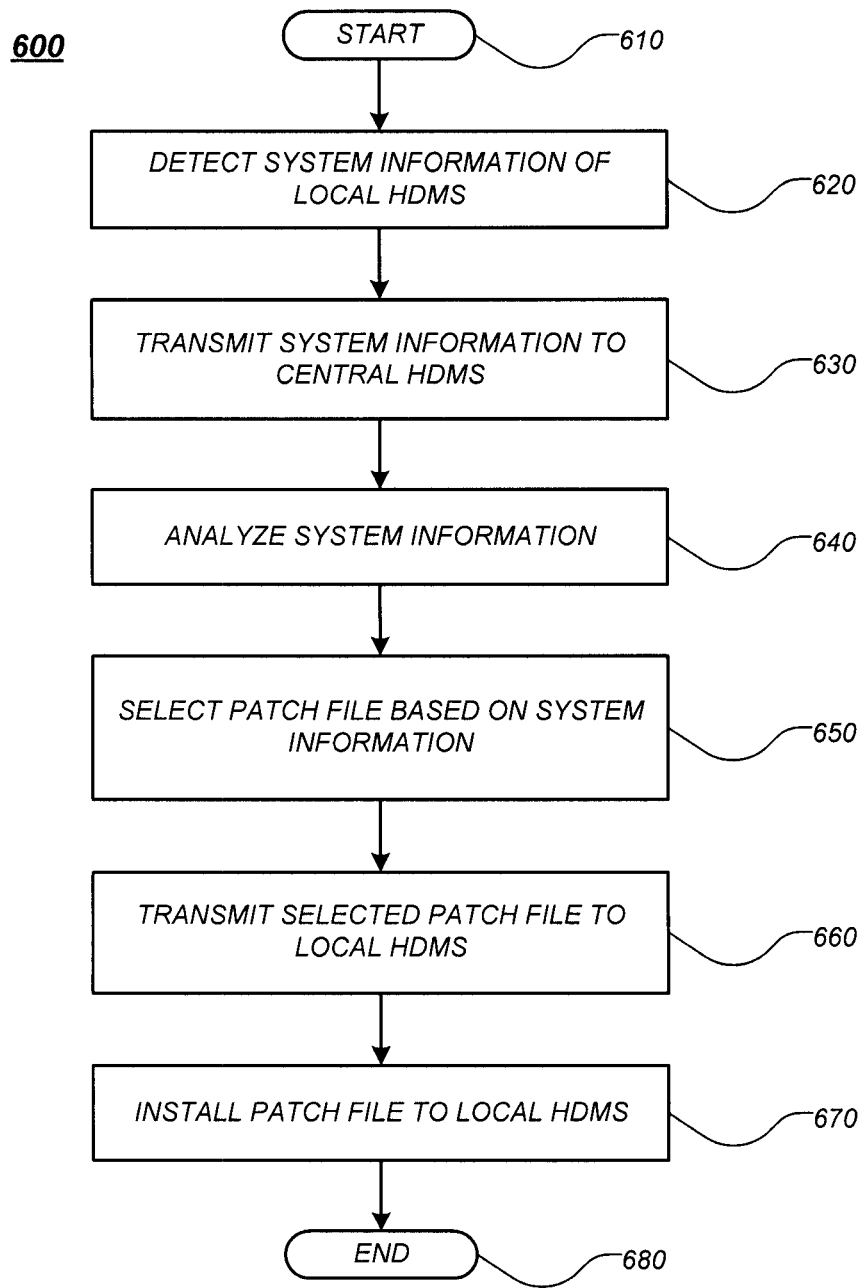
FIG. 6 shows a flowchart of a remote configuration process according to the principles of the disclosure.

FIG. 6 shows a flowchart of a remote configuration process 600 according to the principles of the disclosure. With reference to FIG. 2, the DMA 218 may be configured to detect system information of the local HDMS 200. The system information may include information on devices, drivers and/or the like that are installed or loaded in the local HDMS 200. The system information may further include a type and version of the OS 212, a manufacturer, model and type of the HDMS 200, a type of the central processing unit (CPU), an amount of memory and system resources, a BIOS version, a locale and time zone, a path to the page file and/or the like.

The process 600 may start (at 610) when, for example, the DMA 218 has been installed to the local HDMS 200 for the first time or the DMA 218 has detected a change in the system information of the local HDMS 200. After detecting the system information of the local HDMS 200 (at 620), the DMA 218 may transmit the system information to the central HDMS 10 (at 630). The central HDMS 10 may analyze the system information of the local HDMS 200 (at 640) to determine how to augment and/or modify behaviors of the local HDMS 200.

Based on the analysis of the system information, the central HDMS 10 may select one or more patch files, such as, e.g., a configuration tool file, a library file and/or the like, which may augment and/or modify behaviors of the local HDMS 200 (at 650). The selected patch file or files may be transmitted to the local HDMS 200 via the network 20. As noted above, the central HDMS 10 may send the DMA 218 an instruction to download and install the selected patch file or files. In response to the notification, the DMA 218 may control the local HDMS 200 to download the patch file or files. Upon downloading the patch file or files to the local HDMS 200, the DMA 218 may control the local HDMS 200 to install the patch file or files (at 670) and the process 600 may be terminated (at 680).

According to the disclosure, healthcare data may be safely and securely synchronized between the local healthcare database 230 and the central healthcare database 12 by operating the DMA 218 in the background of the local HDMS 200. Also, by installing the DMA 218, any new or existing computer, PDA and/or the like may be easily converted to a local HDMS 200 and communicate with the central HDMS 10. Further, since the DMA 218 may operate independently from any HPMA 214 that might have been already installed and operating in the existing computers, PDAs and/or the like, any healthcare facilities may easily join the HDN 100 without converting to a new HPMA, increasing the network bandwidth, upgrading computer and network systems and/or the like, which may be costly and time-consuming. Furthermore, the DMA 218 may enable each local HDMS 200 to be remotely maintained, updated, fixed and extended, thereby reducing operational costs for the healthcare facilities and the HDN 100.

In accordance with various embodiments of the disclosure, the methods described herein are intended for operation with dedicated hardware implementations including, but not limited to, semiconductors, application specific integrated circuits, programmable logic arrays, and other hardware devices constructed to implement the methods and modules described herein. Moreover, various embodiments of the disclosure described herein are intended for operation as software programs running on a computer processor. Furthermore, alternative software implementations including, but not limited to, distributed processing, component/object distributed processing, parallel processing, virtual machine processing, any future enhancements, or any future protocol can also be used to implement the methods described herein.

It should also be noted that the software implementations of the disclosure as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the disclosure is considered to include a tangible storage medium or distribution medium, as listed herein and including art-recognized equivalents and successor media, in which the software implementations herein are stored.

While the disclosure has been described in terms of exemplary embodiments, those skilled in the art will recognize that the disclosure can be practiced with modifications in the spirit and scope of the appended claims. These examples given above are merely illustrative and are not meant to be an exhaustive list of all possible designs, embodiments, applications or modifications of the disclosure.

What is claimed is:

1. A method of managing healthcare data, comprising:
collecting healthcare data of at least one patient in a first healthcare database operated by a computer, the computer being controlled by a server;
storing the collected healthcare data in a second healthcare database operated by the server;
detecting changes in the healthcare data of the at least one patient stored in the first healthcare database in real time;
in response to one or more of the detected changes, creating a delta file corresponding to the at least one patient, the delta file including only the one or more detected changes in the healthcare data of the at least one patient and associated minimum information necessary to synchronize the healthcare data between the computer and the server;
in response to each delta file being created, synchronizing the healthcare data between the computer and the server according to the at least one patient, wherein synchronizing healthcare data comprises:
transmitting the delta file to the server; and
updating the healthcare data of the at least one patient stored in the second healthcare database based on the delta file; and
preventing the computer from accessing the collected healthcare data stored in the second healthcare database.

2. The method of claim 1, further comprising:
transmitting a command file from the server to the computer for execution; and
remotely controlling the computer with the server to execute the command file, wherein:
the transmitting the command file comprises transmitting a database query to the computer for execution; and
the remotely controlling the computer to execute the command file comprises remotely controlling the computer to execute the database query against the first healthcare database.

3. The method of claim 1, wherein the healthcare data comprises at least one of personal information, medical records, healthcare provider information, healthcare insurance information, appointment information, diagnosis information, treatment information and prescription information of a patient.

4. The method of claim 1, wherein the computer is configured to manage the healthcare data for one or more local healthcare facilities, and the server is configured to manage the healthcare data for a central healthcare data center.

5. The method of claim 1, further comprising installing a data management agent (DMA) to the computer, wherein the DMA is configured to perform at least one of:
the synchronizing of the healthcare data; and
allowing the server to remotely control the computer to at least one of execute a command file, execute a query against the first healthcare database and optimize a configuration of the computer.

6. The method of claim 1, further comprising:
controlling the computer from the server, the controlling including:
receiving system information associated with the computer;
analyzing the system information associated with the computer with the server;
selecting one or more patch files for the computer based on the system information;
transmitting the one or more patch files from the server to the computer for execution at the computer; and,
remotely controlling the computer to install the one or more patch files in the computer.

7. The method of claim 1, further comprising:
in response to another one or more of the detected changes, creating another delta file corresponding to the at least one patient, the another delta file including only the another one or more detected changes in the healthcare data of the at least one patient and associated minimum information necessary to synchronize the healthcare data between the computer and the server.

8. The method of claim 1, wherein the computer is selected from the group consisting of a desktop computer, a laptop computer, a mobile computer, a netbook, a tablet PC, a personal digital assistant (PDA), a mobile telephone, and a cloud computing configuration.

9. A healthcare data network, comprising:
a computer configured to operate a first healthcare database storing healthcare data of at least one patient, the computer and being controlled by a server; and the server configured to operate a second healthcare database storing the healthcare data collected from the first healthcare database, wherein the computer is configured to perform operations including:

detecting changes in the healthcare data of the at least one patient stored in the first healthcare database in real time, in response to one or more of the detected changes, creating a delta file corresponding to the at least one patient, the delta file including only the one or more detected changes in the healthcare data of the at least one patient and associated minimum information necessary to synchronize the healthcare data between the computer and the server according to the at least one patient, and transmitting each delta file to the server via the network as each delta file is created wherein the computer is prevented from accessing the collected healthcare data stored in the second healthcare database.

10. The healthcare data network of claim 9, wherein the healthcare data comprises at least one of personal information, medical records, healthcare provider information, healthcare insurance information, appointment information, diagnosis information, treatment information and prescription information of a patient.

11. The healthcare data network of claim 9, wherein the computer is further configured to perform the detecting, creating, and transmitting in a background without user intervention.

12. The healthcare data network of claim 9, wherein the computer is remotely controlled by the server to execute a command file.

13. The healthcare data network of claim 9, wherein the computer is remotely controlled by the server to execute a database query transmitted from the server against the first healthcare database.

14. The healthcare data network of claim 9, wherein:

the computer is further configured to:

transmit system information of the computer to the server;

download one or more patch files for the computer from the server; and install the one or more patch files in the computer; and the one or more patch files are selected by the server based on the transmitted system information after analysis of the system information by the server.

15. The healthcare data network of claim 9, wherein the computer is further configured to perform operations including:

in response to another one or more of the detected changes, creating another delta file corresponding to the at least one patient, the another delta file including only the another one or more detected changes in the healthcare data of the at least one patient and associated minimum information necessary to synchronize the healthcare data between the computer and the server.

16. The healthcare data network of claim 9, wherein the computer is selected from the group consisting of a desktop computer, a laptop computer, a mobile computer, a netbook, a tablet PC, a personal digital assistant (PDA), a mobile telephone, and a cloud computing configuration.

17. A system comprising:

a non-transitory program storage medium on which are stored instructions executable by a processor to perform operations for managing healthcare data, the operations including:

detecting changes in healthcare data of at least one patient stored in a first healthcare database of a computer in real time;

in response to one or more of the detected changes, creating a delta file corresponding to the at least one patient, the delta file including only the one or more detected changes in the healthcare data of the at least one patient and associated minimum information necessary to synchronize the healthcare data between the first healthcare database and a second healthcare database of a server;

in response to each delta file being created, transmitting the delta file to the server for updating of the healthcare data of the at least one patient stored in the second healthcare database based on the delta file; and preventing the computer from accessing the healthcare data stored in the second healthcare database.

18. The system of claim 17, further comprising:

the computer; and the server, wherein the computer includes:

the non-transitory program storage medium; and a processor for executing the instructions.

19. The system of claim 17, wherein the operations further include:

in response to another one or more of the detected changes, creating another delta file corresponding to the at least one patient, the another delta file including only the another one or more detected changes in the healthcare data of the at least one patient and associated minimum information necessary to synchronize the healthcare data between the first healthcare database and the second healthcare database.

20. The system of claim 17, wherein the computer is selected from the group consisting of a desktop computer, a laptop computer, a mobile computer, a netbook, a tablet PC, a personal digital assistant (PDA), a mobile telephone, and a cloud computing configuration.

* * * * *